(12) United States Patent
Michael et al.

(10) Patent No.: US 7,745,732 B2
(45) Date of Patent: *Jun. 29, 2010

(54) DRAWN STRAND FILLED TUBING WIRE

(75) Inventors: Mark S. Michael, Corunna, IN (US); Hans-Juergen Wachter, Roedermark (DE); Robert J. Myers, Fort Wayne, IN (US)

(73) Assignees: Fort Wayne Metals Research Products Corporation, Fort Wayne, IN (US); W.C. Heraeus GmbH & Co. KG, Hanau (DE)

(*) Notice: Subject to any disclaimer, the term of this patent is extended or adjusted under 35 U.S.C. 154(b) by 0 days.

This patent is subject to a terminal disclaimer.

(21) Appl. No.: 12/361,759

(22) Filed: Jan. 29, 2009

(65) Prior Publication Data

US 2009/0133899 A1 May 28, 2009

Related U.S. Application Data

(63) Continuation of application No. 11/203,986, filed on Aug. 15, 2005, now Pat. No. 7,501,579, which is a continuation-in-part of application No. 10/524,387, filed as application No. PCT/US2004/029957 on Sep. 13, 2004, now Pat. No. 7,420,124.

(60) Provisional application No. 60/543,740, filed on Feb. 11, 2004.

(51) Int. Cl.
*H01B 5/00* (2006.01)
(52) U.S. Cl. .............. 174/126.1; 174/125.1; 174/128.1
(58) Field of Classification Search .......... 174/126.1, 174/126.2, 128.1, 128.2
See application file for complete search history.

(56) References Cited

U.S. PATENT DOCUMENTS

| 2,050,298 | A | 8/1936 | Everett |
| 3,474,187 | A | 10/1969 | Donadieu et al. |
| 3,760,092 | A | 9/1973 | Woolcock et al. |
| 4,078,299 | A | 3/1978 | Fuuto et al. |
| 4,273,137 | A | 6/1981 | Pravoverov et al. |
| 4,559,951 | A | 12/1985 | Dahl et al. |
| 4,646,428 | A | 3/1987 | Marancik et al. |
| 4,863,804 | A | 9/1989 | Whitlow et al. |
| 5,170,802 | A | 12/1992 | Mehra |
| 5,224,491 | A | 7/1993 | Mehra |
| 5,283,232 | A | 2/1994 | Kohno et al. |

(Continued)

FOREIGN PATENT DOCUMENTS

EP 0408358 A2 1/1991

(Continued)

OTHER PUBLICATIONS

The Supplementary European Search Report mailed Dec. 14, 2009 in related European Patent Application No. 04783973.3.

*Primary Examiner*—Chau N Nguyen
(74) *Attorney, Agent, or Firm*—Baker & Daniels LLP

(57) ABSTRACT

A wire for use in medical applications. The wire is formed by forming a bundle from a plurality of metallic strands and positioning the bundle within an outer tube. The tube and strands are then drawn down to a predetermined diameter to form a wire for use in medical devices. The wire may be covered with an insulating material.

17 Claims, 8 Drawing Sheets

U.S. PATENT DOCUMENTS

| | | | |
|---|---|---|---|
| 5,324,328 | A | 6/1994 | Li et al. |
| 5,330,521 | A | 7/1994 | Cohen |
| 5,360,442 | A | 11/1994 | Dahl |
| 5,483,022 | A | 1/1996 | Mar |
| 5,630,840 | A | 5/1997 | Mayer |
| 5,716,391 | A | 2/1998 | Grandjean |
| 5,755,760 | A | 5/1998 | Maguire et al. |
| 5,760,341 | A | 6/1998 | Laske et al. |
| 5,796,044 | A | 8/1998 | Cobian et al. |
| 5,871,531 | A | 2/1999 | Struble |
| 5,935,159 | A | 8/1999 | Cross, Jr. et al. |
| 6,168,570 | B1 | 1/2001 | Ferrera |
| 6,307,156 | B1 | 10/2001 | Avellanet |
| 6,399,886 | B1 * | 6/2002 | Avellanet ............ 174/128.1 |
| 6,497,671 | B2 | 12/2002 | Ferrera et al. |
| 6,516,230 | B2 | 2/2003 | Williams et al. |
| 6,616,617 | B1 | 9/2003 | Ferrera et al. |
| 6,720,497 | B1 | 4/2004 | Barsne |
| 7,065,411 | B2 | 6/2006 | Verness |
| 7,138,582 | B2 | 11/2006 | Lessar et al. |
| 7,280,875 | B1 | 10/2007 | Chitre et al. |
| 7,420,124 | B2 * | 9/2008 | Michael et al. .......... 174/126.1 |
| 7,501,579 | B2 * | 3/2009 | Michael et al. .......... 174/126.1 |
| 2002/0133180 | A1 | 9/2002 | Ryan et al. |
| 2003/0032997 | A1 | 2/2003 | Pianca et al. |

FOREIGN PATENT DOCUMENTS

| | | | |
|---|---|---|---|
| JP | 62-071113 | A | 4/1987 |
| JP | 62-188110 | A | 8/1987 |
| JP | 2000-225643 | A | 8/2000 |
| JP | 2002-501402 | T | 1/2002 |

* cited by examiner

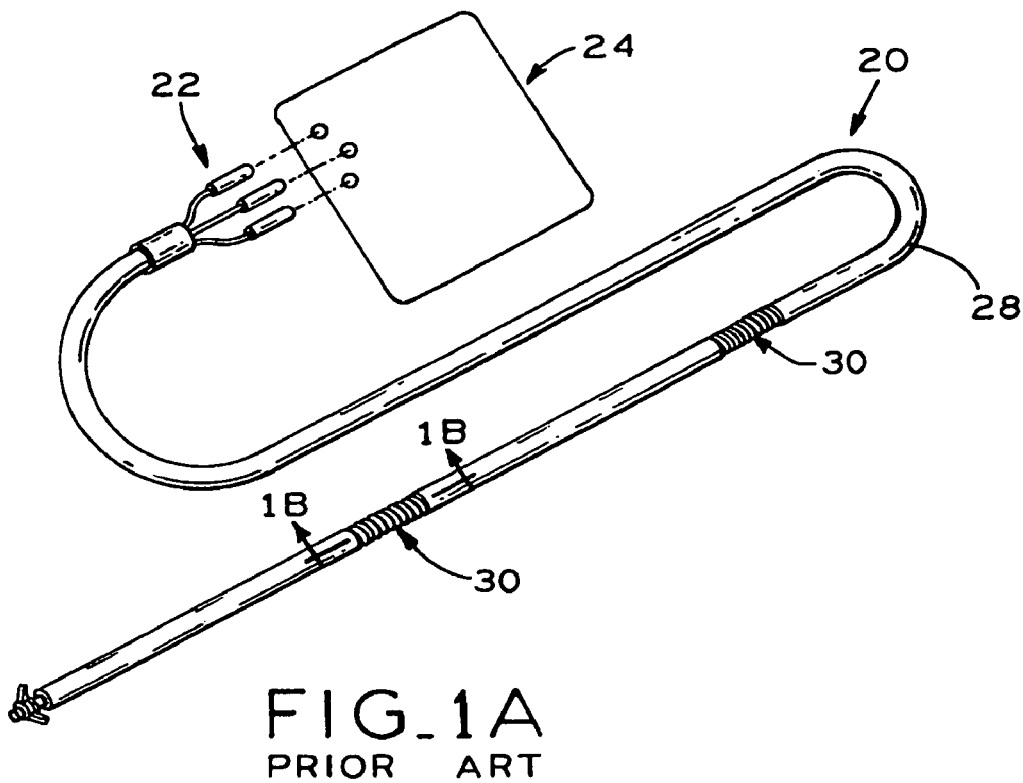
FIG_1A
PRIOR ART
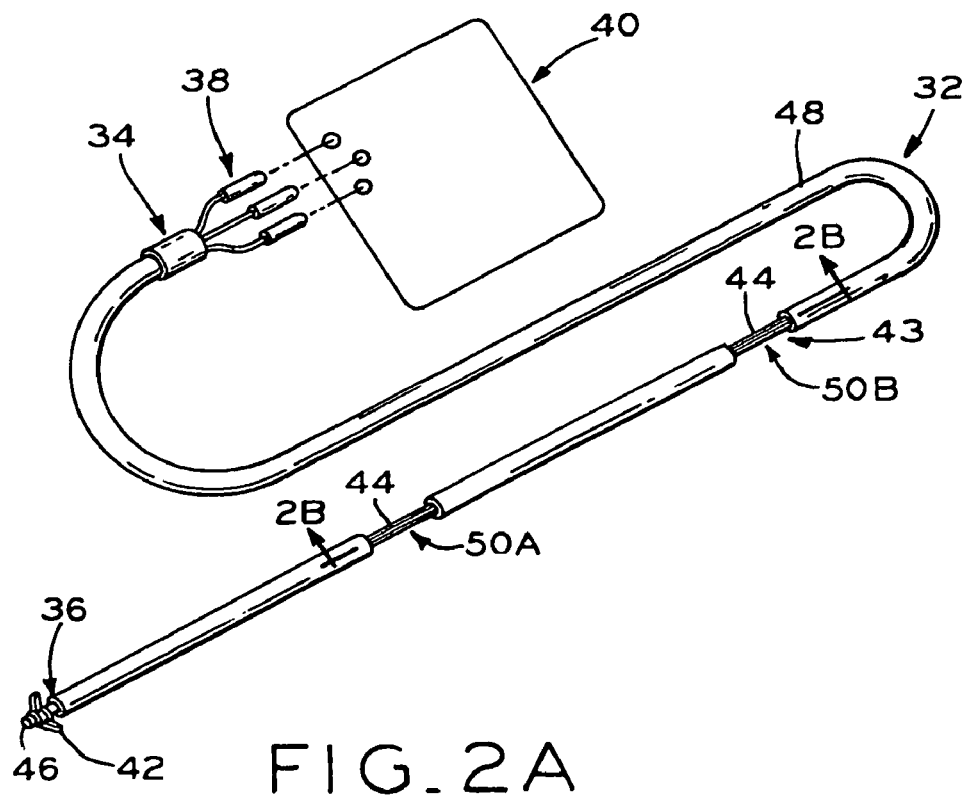
FIG_2A

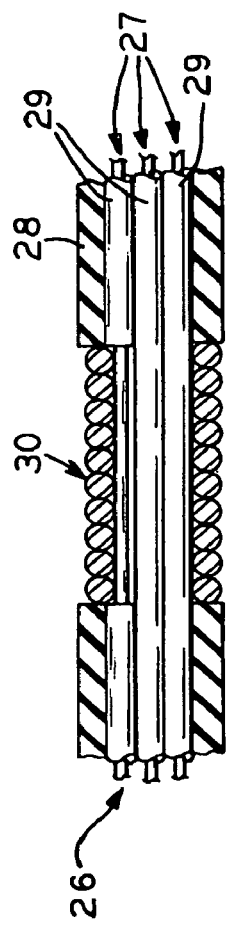
FIG_1B
PRIOR ART
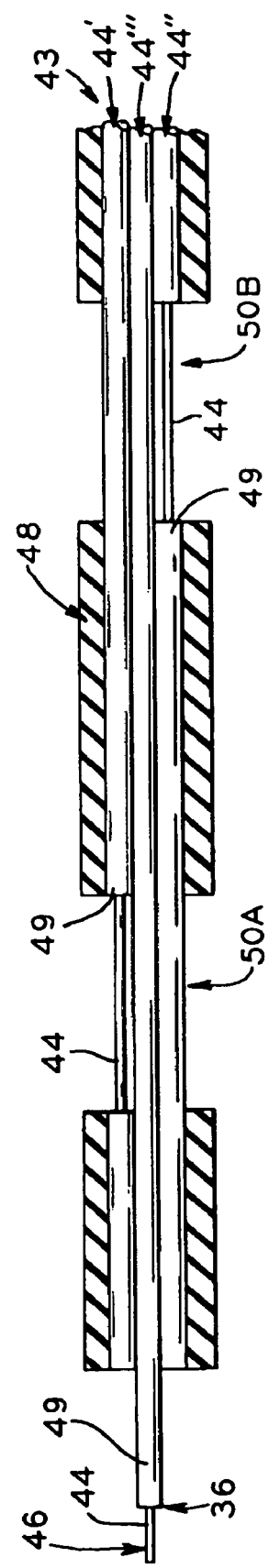
FIG_2B

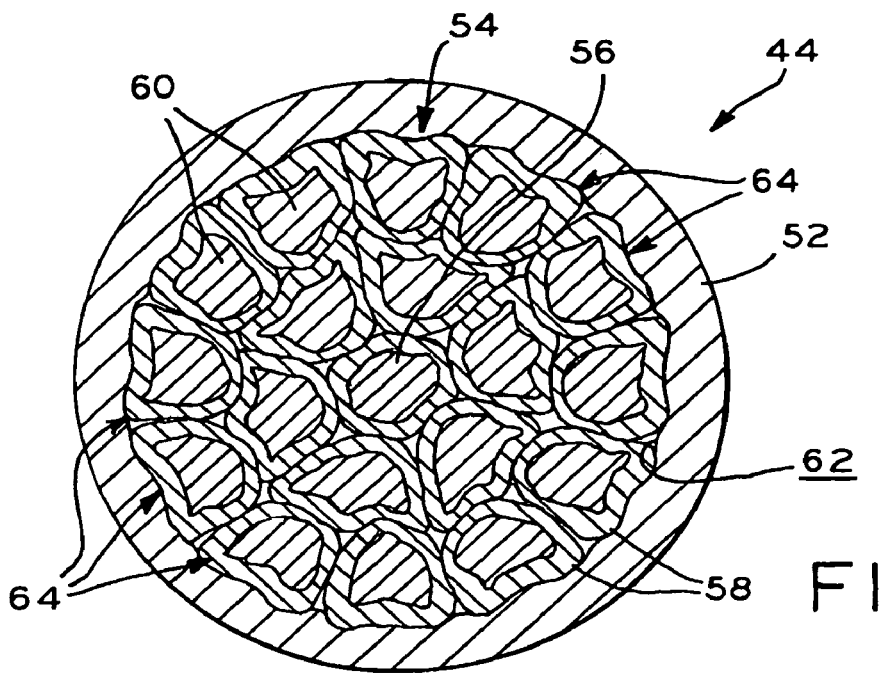
FIG_5
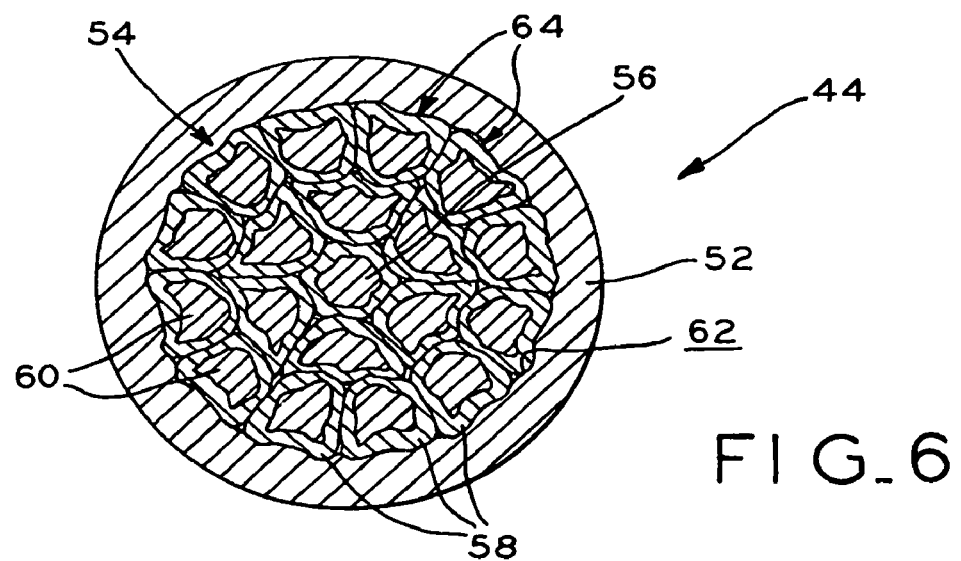
FIG_6
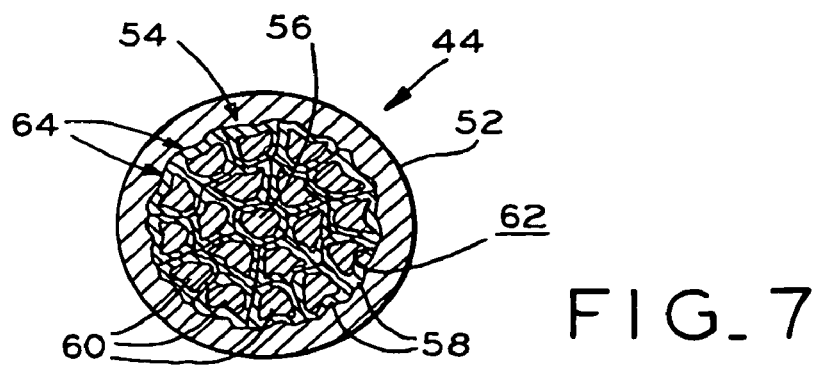
FIG_7

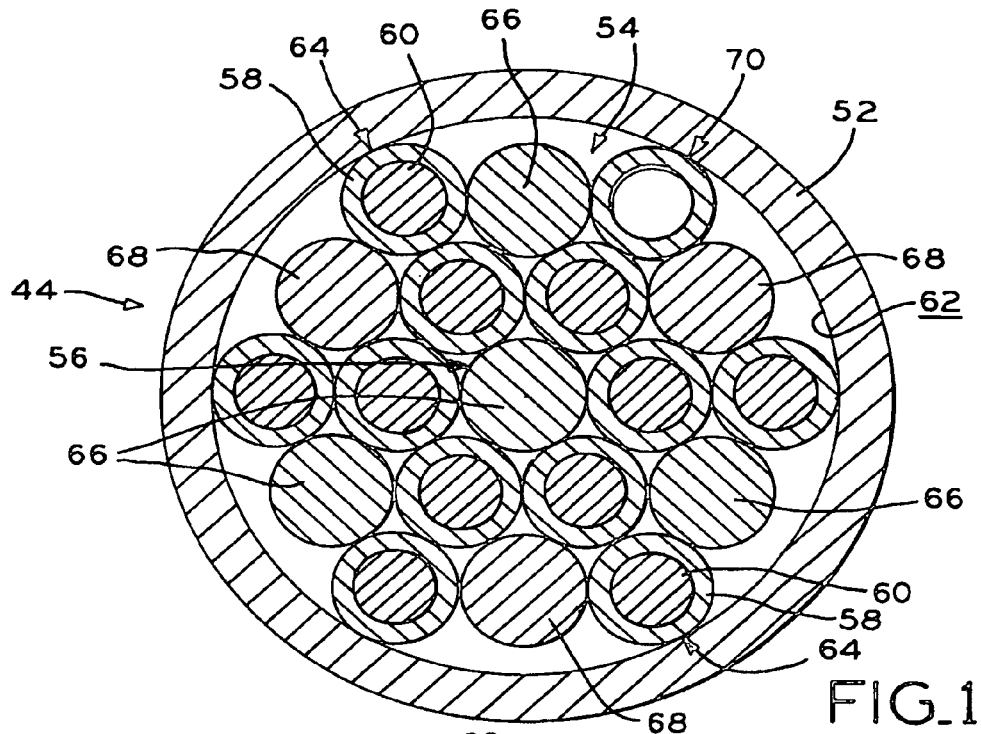
FIG_10
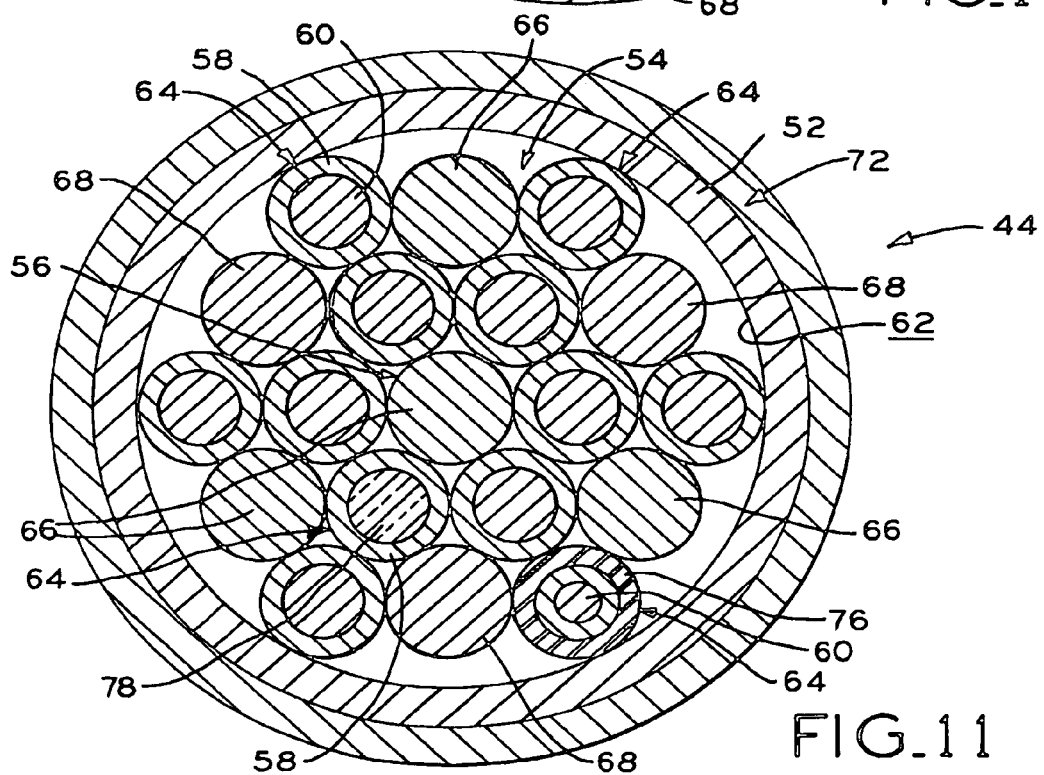
FIG_11

DRAWN STRAND FILLED TUBING WIRE

CROSS-REFERENCE TO RELATED APPLICATION

This application is a continuation of U.S. patent application Ser. No. 11/203,986, filed Aug. 15, 2005, now U.S. Pat. No. 7,501,579, which is a continuation-in-part of U.S. patent application Ser. No. 10/524,387, filed Oct. 3, 2005, now U.S. Pat. No. 7,420,124, which is related to and claims the benefit under 35 U.S.C. 119 and 35 U.S.C. 365 of International Application PCT/U52004/029957, filed Sep. 13, 2004, now Publication No. WO 05/081681, which is a non-provisional application of U.S. provisional application Ser. No. 60/543,740, filed Feb. 11, 2004. The disclosures of each of the foregoing references are explicitly incorporated by reference herein.

BACKGROUND OF THE INVENTION

1. Field of the Invention

The present invention relates to a drawn strand filled tubing wire for use in medical applications and in particular to such wire where there is a need to apply an electrical voltage to human tissue.

2. Description of the Related Art

Implantable devices used in the medical field for applying electrical voltage are customarily meant to stay implanted for several years. Such devices are used as pacing leads, for example. These medical devices must possess several characteristics including electrical conductivity, corrosion resistance, and biocompatibility. The medical devices generally need to be flexible for snaking through arteries, for example.

Drawn filled tubing wire is a type of wire that has been used extensively in medical devices. This wire includes an outer shell that is filled with an electrically conductive material. While the materials used for the outer shell are strong, they tend to be susceptible to corrosion when contacted by body tissues and fluids. Therefore, drawn filled tubing wire for medical use is customarily coated with an insulating material such as silicone to prevent contact with human body tissue. Pacing leads for applying an electric potential to the heart usually comprise two or three drawn filled tubing wires. Such leads are described in U.S. Pat. Nos. 5,716,391, 5,755,760, 5,796,044, and 5,871,531. A portion of the wires in such leads is generally encased within a biocompatible material such as platinum, tantalum filled platinum, tantalum filled platinum-iridium, or the like to allow an electrical voltage to be applied from the wire to the desired tissue area. A problem with such biocompatible materials is that they have insufficient strength and have limited electrical conductivity, and therefore must be combined with the wire.

Referring to FIGS. 1A and 1B, a prior art pacing lead is shown for use in medical applications. Implantable cardio defibrillator (ICD) 20 is used for sensing electrical activity in the heart and for delivering a shock if heart activity slows or stops. ICD 20 is implantable and has flexible, elongated conductive lead 26 (FIG. 1B) with electrical connector 22 extending from one end thereof to plug into control 24 for controlling ICD 20 and for providing the electrical supply. Control 24 is implanted just beneath the skin, often in the chest or abdomen.

Lead 26 is constructed from two or three electrically conductive wires 27 such as wires having an alloy exterior tube filled with highly conductive silver, for example. Each wire 27 is substantially covered with insulating material 29. Lead 26 is then substantially covered with insulating material 28. At two locations along lead 26, coils 30 are located which are made from a biocompatible material such as platinum, tantalum filled platinum, tantalum filled platinum-iridium, or the like. Coils 30 are secured to individual wires 27 of lead 26 by any suitable process including laser welding. The portion of wire 27 in contact with coil 30 has insulating material 29 removed to allow for the welding process. These coils 30 form the contacts which engage the heart tissue at specific locations to deliver an electrical voltage, when control 24 senses the need to deliver such voltage.

The interface between insulating material 28 and coils 30 must be hermetically sealed to prevent fluids from contacting wires 27 of lead 26 and causing corrosion and possible eventual failure of the ICD. Problems exist in that the achieving a hermetic seal of a polymeric material and a metal is difficult and costly. The bond may be susceptible to corrosion and bodily fluid leaking into the area between coil 30 or insulating materials 28, and wires 27 of lead 26. In addition, the materials used to form coils 30 are very flexible and may be easily damaged simply from handling the coils. The welding process between wires 27 of lead 26 and coils 30 is a further step in the manufacturing process which increases the cost of production of ICD 20.

In the medical device industry, leads are used to transmit an electrical voltage from an electrical supply source to an area in a human body. The lead interfaces with tissues in the body so that an electrical signal may be introduced to a particular area of the body. Such leads may be implanted in a patient at any location in the body where the electrophysiology needs to be monitored and/or artificially altered. Specific applications may be implantable defibrillators or pacing leads. The leads may also be used for pain relief or pain suppression in the back or spine relating to diseases such as Parkinson's disease. The lead may be further implanted in the stomach to subside hunger pains. For patients with neurological damage, the leads might be used to replace the nerve and act to transmit electrical signals from one place to another in the body. These devices are most certainly used in humans however, they are not limited to humans and may be adapted for use in animals.

The devices are designed for long term implantation and must have several properties including resistivity, corrosion resistance, radiopacity, reliability, stiffness, fatigue life, weldability, MRI compatibility, and biocompatibility. Other characteristics of the device include a predetermined ultimate tensile strength, Young's modulus, level of inclusions, fracture toughness, and percent elongation. In addition, the types of materials used, the construction, and the cost of manufacturing the device are all factors.

It is therefore an object of the present invention to provide a pacing lead with improved wires which eliminate the need for conductive coils.

It is therefore a further object of the present invention to reduce the risk of corrosion of the pacing lead.

It is therefore another object of the present invention to improve conductivity and flexibility of the pacing lead.

SUMMARY OF THE INVENTION

The present invention provides a wire for use in accomplishing the objects set out hereinabove. The wire includes a plurality of strands, wires, or elements of material which are arranged in a particular orientation and are twisted or braided into a bundle before being positioned within an outer tube. The strands are formed from any of a plurality of materials to define the mechanical and electrical characteristics of the device. Such characteristics include corrosion resistance, strength, electrical conductivity, radiopacity, reliability, stiffness, fatigue life, weldability, MRI compatibility, biocompatibility and the like. In addition, a hollow strand may be used to allow for fluid transfer along the length of the device for use in drug delivery to the patient, for example. Alternatively, a fiber optic strand could be included as well as electrically insulated strands. The tubing and strands are then drawn to a predetermined diameter to form a wire for use in medical devices. The wire may be covered with an insulating material.

An advantage of the present invention is that by use of the present invention, the need for conductive coils in pacing leads is eliminated.

Another advantage of the present invention is that the risk for corrosion of the wires used in pacing leads and the like is significantly reduced.

Yet another advantage of the present invention is that by using a wire having a plurality of strands or elements within the outer tubing, the wire is more flexible and is less subject to mechanical failure due to fatigue than prior art wires.

Still another advantage is a wire with improved conductivity and lower battery consumption when used in pacing leads.

Yet still another advantage is a wire which is more comfortable to the patient.

A yet further advantage is that the wire would be more reliable as, even if one strand were to fail, there are numerous strands within the wire which would not fail, i.e., the strands have redundancy.

A yet another advantage of the wire is that it would provide design flexibility.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 1A is a perspective view of a prior art implantable cardio defibrillator using materials in accordance with the prior art.

FIG. 1B is a sectional view of FIG. 1A taken along line 1B-1B.

FIG. 2A is a perspective view of an implantable cardio defibrillator using a lead in accordance with the present invention.

FIG. 2B is a sectional view of FIG. 2A taken along line 2B-2B.

FIG. 5 is a sectional view of the assembled plurality of strands and outer tubing of FIG. 4 after drawing of the assembly.

FIG. 6 is a sectional view of the assembled plurality of strands and outer tubing after drawing of the assembly to a smaller diameter than that shown in FIG. 5.

FIG. 7 is a sectional view of the assembled plurality of strands and outer tubing after drawing of the assembly to a smaller diameter than that shown in FIG. 6.

FIG. 10 is a sectional view of a third arrangement of a plurality of strands assembled with an outer tubing.

FIG. 11 is a sectional view of a fourth arrangement showing the plurality of strands assembled with an outer tubing FIG. 9 located within a second outer tubing.

Figure 3:
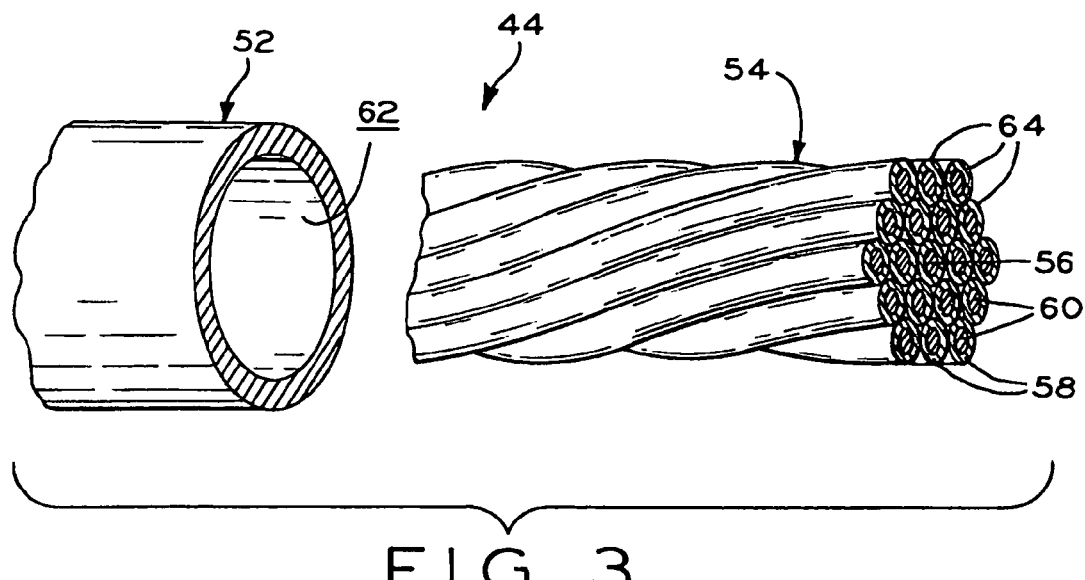
FIG. 3 is an exploded perspective view of a plurality of twisted strands assembled within a tube.

Corresponding reference characters indicate corresponding parts throughout the several views. Although the exemplification set out herein illustrates the invention, the embodiments disclosed below are not intended to be exhaustive or to be construed as limiting the scope of the invention to the precise forms disclosed.

DESCRIPTION OF THE PRESENT INVENTION

Referring to FIG. 2A, one example of a device utilizing the lead formed in accordance with the present invention is illustrated. Implantable cardio defibrillator (ICD) 32 includes an elongated lead used to shock the heart when the heart rate becomes irregular. ICD 32 has first end 34 and second end 36. First end 34 is provided with electrical connectors 38 which engage control 40 which includes an electrical supply or battery pack. Control 40 is implanted just beneath the skin of the patient and is designed to have a long life so that frequent removal and replacement is unnecessary. Second end 36 is mounted in the area of the body being sensed which, in this example, is the heart. Second end 36 is provided with barbs 42 which anchor the end of ICD 32 in place. Lead 43 extends the length of ICD 32 and includes three wires 44. End 46 of one wire 44 has barbs 42 mounted thereon and is exposed. Wire end 46 acts as a sensor to monitor the heart's activity and initiate shock treatments to the heart when necessary.

Referring to FIGS. 2A and 2B, lead 43 is covered with a layer of insulating material 48 which may be formed from any suitable, biocompatible material such as, for example, urethane, to electrically insulate the conductor. Insulating material 48 substantially extends the length of lead 43 with the exception of wire end 46 and contact sections 50A and 50B. One wire 44 of lead 43 is exposed to the body tissues at end 46 and at each contact sections 50A and 50B so as to interface with the body tissues and deliver an electrical shock as necessary. By using three wires to define three electrical contact points along lead 43, electrical potential is created between end 46, and contact sections 50A and 50B. Contact sections 50A and 50B are spaced apart a predetermined distance which coincides with the anatomy of the particular patient.

Figure 4:
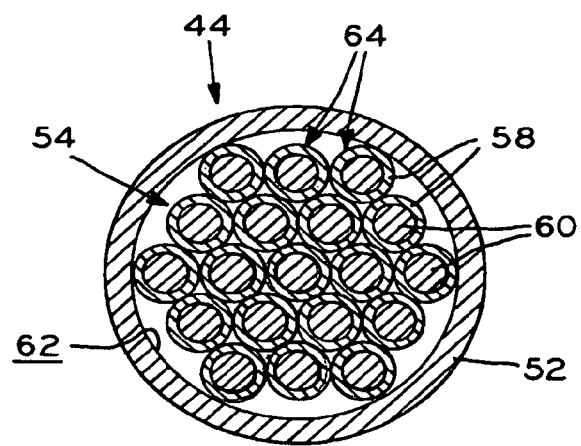
FIG. 4 is a sectional view of the assembled plurality of twisted strands and outer tube of FIG. 3.

Referring now to FIGS. 3 and 4, wire 44 is constructed such that it acts as both the electrical contact surface and the electrical lead, thus making coils 30 of FIG. 1A unnecessary for providing the interface between the conductor and the body tissue. Thus, corrosion at the urethane to metal joint of FIG. 1B between insulating material 28 and coils 30 is eliminated. In addition, since fragile coils 30 are also eliminated, the cost of assembly and materials is reduced.

Wire 44 comprises drawn strand filled tubing wire formed from outer tubing 52 and a plurality of strands, elements or wires 54. Each of the strands may comprise a drawn filled tube wire. The initial size of the strand diameter may be in the range of 1 mm-11 mm. The plurality of strands 54 are twisted or braided into a braided bundle as shown in FIG. 3 with the outer strands being rotated about center strand 56. The twisted plurality of strands 54 is positioned within outer tubing 52 and the conductor is thereafter drawn to the desired diameter. The twisting of strands 54 into a braided bundle ensures that wire 44 has the correct orientation of strands 54 throughout its length after being drawn. As wire 44 is drawn, strands 54 are lengthened and align in the predetermined arrangement. The diameter of drawn outer tubing 52 may be in the range of 2-12 mm, for example, but may be smaller for certain applications.

There are several advantages to using strands 54 inside tubing 52. Strands 54 provide a more flexible wire 44 which is an important factor when snaking wire 44 through the patient's arteries, for example. The more strands 54 used, the greater the flexibility. Additionally, overall fatigue life is improved for wire 44. For example, if one strand 54 has a crack initiated at a high stress point or stress riser so strand 54 ultimately fails, fatigue must be reinitiated in another of strands 54 until all of strands 54 fail before wire 44 fails completely, thus improving the life of wire 44.

Wire 44 is a metal-to-metal composite that combines the desired physical and mechanical properties of two or more materials into a single lead. Wire 44 is drawn at ambient temperature. However, as the drawing process occurs, the temperature and pressures increase significantly causing the formation of mechanical bonds between strands 54 and outer tubing 52. By using the drawn strand filled tube technology, dissimilar materials may be combined to provide a variety of properties in a single conductor 54. The composite then has an outer tubing layer 52 which is biocompatible and electrically conductive while the core material is designed to provide strength, conductivity, radiopacity, resiliency, MRI enhancement, or the like.

In the embodiments shown in the figures, wire 44 is provided with 19 strands 54. The number of strands 54 however may be any desired number to fill tubing 52, or to provide particular properties to wire 44 as will be discussed further hereinbelow. The diameter of the individual strands 54 also determines the number of strands used to fill outer tubing 52. In addition, the number of strands 54 directly relates to the cost of wire 44.

Outer tubing 52 is constructed from a biocompatible material so that the necessary electrical contact is made directly between wire 44 and body tissues. Such materials may include platinum or platinum alloys, tantalum or tantalum alloys, tantalum filled platinum, tantalum filled platinum-iridium, or the like. Outer tubing 52 has a thickness which is dependent upon the type of wire 44 which is desired. The thicker the wall of outer tubing 52, the more rigidity it provides to wire 44. If the wall of outer tubing 52 is made thinner, wire 44 is more flexible and the cost of materials is reduced. The outer tubing however, should not be made too thin so as to risk compromising the outer wall of wire 44.

Referring to FIG. 4, a first embodiment of wire 44 is illustrated having identical strands 54. In this instance, strands 54 comprise drawn filled tubing wires. Strand 54 is a metal to metal composite comprising an outer tubing 58 formed from any suitable material possessing the characteristics desired in wire 44. One such material may be a cobalt-nickel-chromium alloy known as ASTM Standard F562. The ASTM F562 material has characteristics including strength and long fatigue life. The strands 54 are filled with silver 60 because silver is ductile and malleable, and has very high electrical and thermal conductivity. One acceptable type of strand is filled with 41 percent silver by weight. However, any suitable amount of silver or other suitable conductor may be used. For example, if 60 percent silver, by weight, is used in the strands, the strands have higher electrical and thermal conductivity. However, less ASTM F562 is then used and the strength of the strand is reduced. The combination of metals is ultimately determined by the desired properties for each strand 64. An alternative material which may be used in place of ASTM F562 material is a similar alloy. In addition to ASTM F562 materials such as ASTM Standard F90, F538, and other nickel, cobalt based super alloys, titanium, nitinol such as ASTM F2063, and tantalum materials may be used. A material which has a much longer fatigue life than ASTM F562 and which is described in U.S. patent application, entitled "Cobalt Nickel Chromium Molybdenum Alloy With A Reduced Level Of Titanium Nitride Inclusions," filed Sep. 5, 2003, the disclosure of which is hereby incorporated herein by reference, may also be useful in particular applications of lead 44.

Once the strands 54 are positioned within outer tubing 52, wire 44 is drawn to reduce the diameter to the desired size. Referring to FIGS. 5, 6, and 7, wire 44 is illustrated in stages as it is drawn to a small diameter. As the conductor is drawn, the strands 54 impinge upon one another and inner surface 62 of outer tubing 52. The round shape of each strand 54 is compromised by being compressed into adjacent strands 54 and inner tubing surface 62. The material used for outer tubing 52 is relatively ductile compared to ASTM F562, for example, which is why inner tubing surface 62 becomes deformed as outer tubing 52 is compressed against strands 54. The thickness of outer tubing 52 further depends upon the ability of the tubing material to apply forces against strands 54 to compress and deform the strands without compromising the outer tubing.

Referring to FIG. 7, center strand 56 has a substantially hexagonal cross section while the rest of strands 54 have non-hexagonal cross sections because they are in the transition area between the core and inner tubing surface 62. If the number of strands 54 is increased, the layers of strands surrounding center stand 56 would increasingly show a substantially hexagonal cross section, the hexagonal shape migrating from center strand 56 toward the outer transition layers.

In order to eliminate some of the deformation of inner tubing surface 62, outer strands 54 could be swaged to develop facets which would engage surface 62. The interface between strands 54 and inner tubing surface 62 may then be preserved due to the more uniform pressure being exerted between strands 54 and outer tubing 52. This may help to reduce the risk of compromising a thinner walled outer tubing 52.

After wire 44 has been drawn to an appropriate length or cut from a roll of drawn strand filled tubing wire, for example, insulating material 49 (FIG. 2B) is applied to the outer surface of outer tubing 52. Insulating material 49 is applied to each wire 44 in any suitable manner to electrically insulate wires 44 and define the three contact points with the body, sensor 46 and both contact sections 50A and 50B. Referring to FIG. 2B, a portion of insulating material 49 is removed from wire 44' to define contact section 50A with the other two wires 44" and 44''' remaining completely insulated at contact section 50A. Similarly, a portion of insulting material 49 is removed from wire 44" to define contact section 50B. Insulating material 49 is removed at contact end 46 of wire 44''' to provide a sensor. The thickness of insulating material 49 can be reduced since the sealing engagement between insulating material 28 and coils 30 of the prior art is eliminated. This sealing engagement is provided to prevent fluids from coming into contact with conductor 20 of the prior art. By completely encasing the inner, electrically conductive portion or strands 54 with a biocompatible outer tubing 52, the risk of contact of fluids with strands 54 is substantially eliminated. Thinner coatings of insulating material 49 makes wires 44 and thus lead 43 more pliable, allowing for easier insertion into a patient.

In addition, the manufacturing of wire 44 may be simplified by the elimination of coils 30. Insulating material 49 is simply removed from wire 44 at sensor 46 and contact sections 50A and 50B to expose wire 44. Alternatively, sleeves of insulting material 49 may be positioned about the outer surface of outer tubing 52 and drawn down with wire 44.

When constructing lead 43, insulating material 48 is then applied to the bundle of three wires 44', 44", and 44'", by any suitable method so as to insulate and contain wires 44 while exposing the electrical contact areas sensor 46, and contact sections 50A and 50B. Insulating material 48 also maintain the orientation of the wires, keeping the exposed portions of wires 44 aligned with the openings defining contact sections 50A and 50B in insulating material 48.

Figure 8:
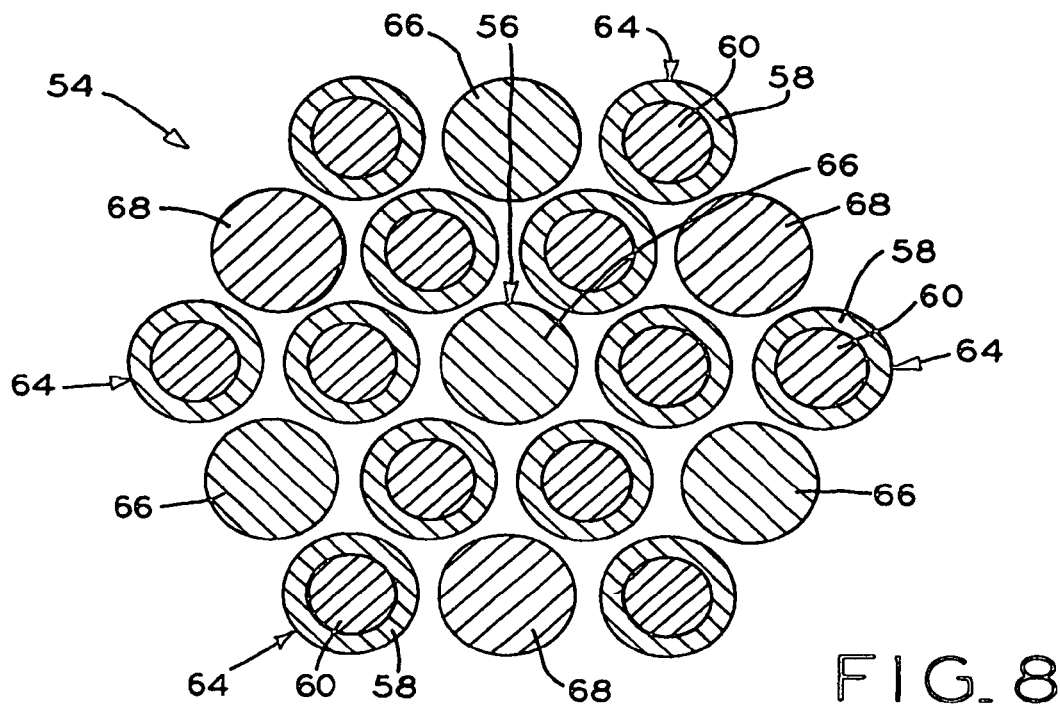
FIG. 8 is a sectional view of an alternative arrangement of a plurality of strands.
Figure 9:
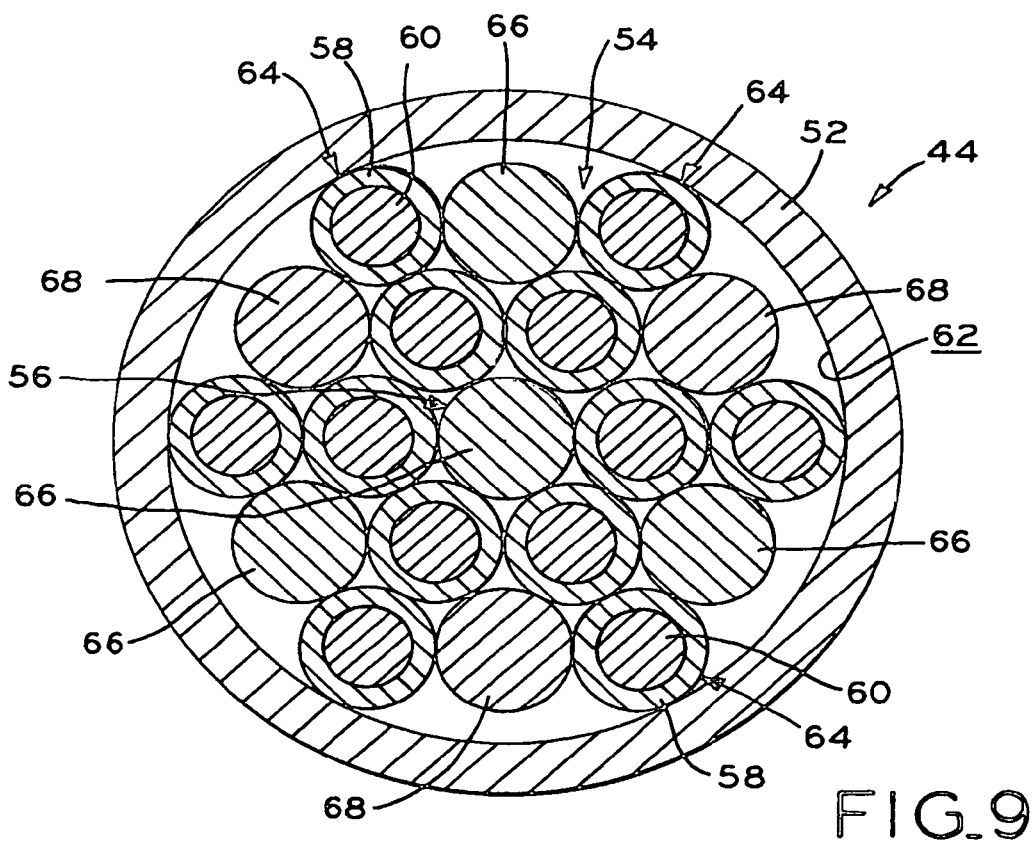
FIG. 9 is a sectional view of the alternative arrangement of FIG. 8 located in an outer tubing.

Strands 54 located in outer tubing 52 may include various types of materials to provide specific mechanical attributes to wire 44. Referring to the embodiment shown in FIGS. 8 and 9, several of strands 54 are strands 64 as in the previous embodiment. The inner silver 60 of strands 64 provides electrical conductivity through wire 44 while outer tubing 58 adds strength. To further strengthen wire 44 and improve fatigue life, solid strands 66 of materials including ASTM F562, and the like may be included in the plurality of strands 54. Other properties may be specifically addressed in wire 44 by adding different types of strands 54. For example, by adding solid platinum or tantalum strands 68, radiopacity of wire 44 is enhanced. Tungsten has excellent corrosion resistance and may be added to improve that particular property of wire 44. Ultimately, any types of strands 54 may be combined to create a lead 44 have predetermined properties.

An alternative method of building the stiffness of wire 44 as shown in FIG. 11 would be to position strands 54 within a first tube of a material such as ASTM F562, for example, and then to position the ASTM F562 or strand filled tube wire in second, outer tubing 72 having the properties required of outer tubing 52. Second tubing 72 would be of a material such as platinum, tantalum filled platinum, tantalum filled platinum-iridium, or the like, all of which are biocompatible and electrically conductive. The entire assembly could then be drawn to the desired diameter. Further, second outer tubing 72 could be in the form of a strip which is wrapped around first tube 52 and laser welded.

Referring to FIG. 10, a further embodiment is illustrated in which one of strands 54 is a tubular, hollow strand 70. Hollow strand 70 would allow for passage of fluid through wire 44 which may be useful for applications involving drug delivery, for example.

Further, FIG. 11 also shows a DFT strand 64 which includes a silver core 64, tubing 58, and an insulation layer 76. Additionally, FIG. 11 shows a strand 64 with a glass, fiber optic, core 78 and a metallic tubing 58. If desired, the tubing 58 could be deleted from core 78.

Figure 12:
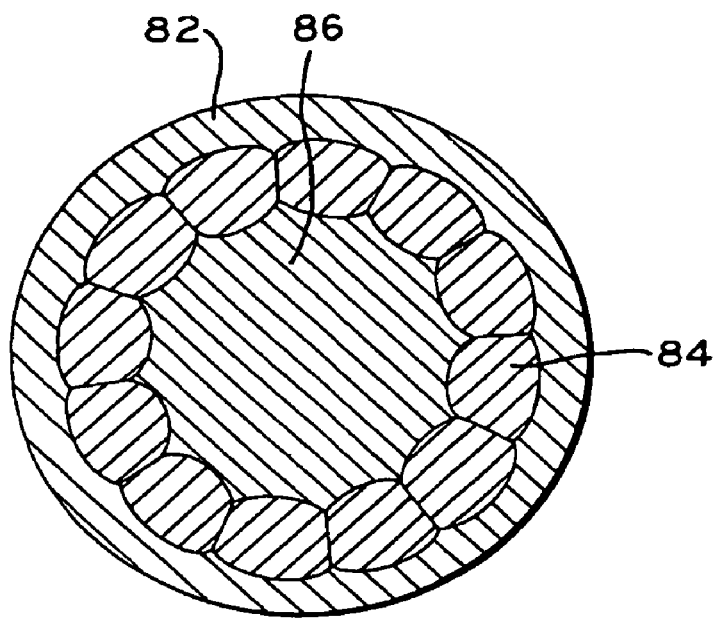
FIG. 12 is a sectional view of a fifth arrangement showing a tube containing a plurality of strands which surround a core.

Referring to FIG. 12, a further embodiment is illustrated having an outer shell or tube 82 composed of a platinum alloy containing 10% iridium. Inside tube 82 is a central core 86 formed of tantalum RO5200 elements or strands of material surrounded by strands 84 of 35NLT material. The wire product is manufactured by first forming the stranded tantalum bundle 86, then surrounding the tantalum elements or strands with strands 84 of 35NLT and then inserting the composite bundle of strands into a tube 82 and drawing down the tube 82 and its contents to form the product as shown in FIG. 12. It should be noted that no voids are present within the tubular structure, the tantalum strands or filaments 86 are tightly packed together. Furthermore, the 35NLT strands or elements 84 are tightly packed together.

It should be noted that in this description the words strand and filament are used interchangeably.

Figure 13:
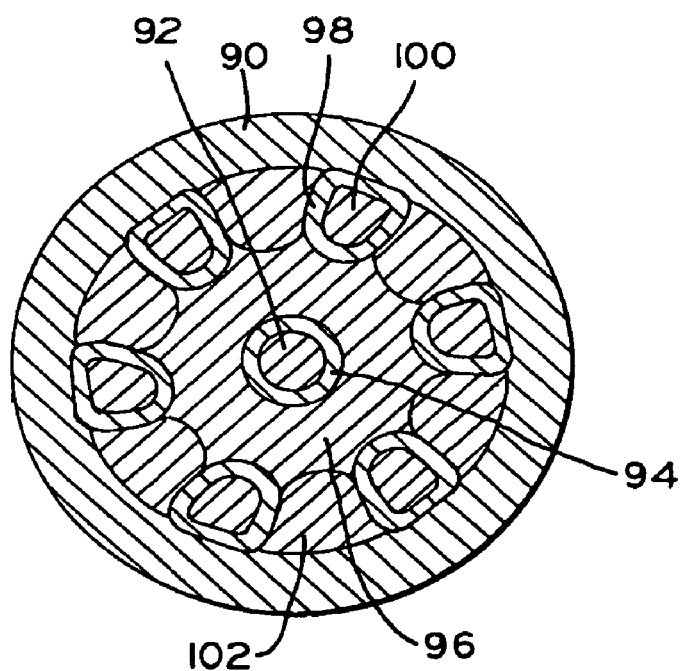
FIG. 13 is a sectional view of a sixth arrangement showing a tube containing a core which is contained in a second tube and which is in turn surrounded by strands and filled tubes.

FIG. 13 shows a still further embodiment wherein an outer shell 90 is composed of a platinum alloy containing 10% iridium. The core of this structure is composed of a 41% silver material 92 enclosed within a 35NLT tube 94. Tube 94 and silver material 92 may comprise a drawn filled tube (DFM™). Surrounding tube 94 are six silver strands or filaments 96 which are wrapped around tube 94. Surrounding silver strands 96 are twelve filaments or strands consisting of alternating tantalum RO5200 strands 102 and drawn filled tubes 98 composed of 35NLT tubes 98 filled with a metal material containing 41% silver 100. The entire structure is manufactured by first forming a composite stranded or braided cable composed of elements 92, 94, 96, 98, 100, and 102, enclosing the stranded cable within tube 90, and thereafter drawing down the tube 90 and the enclosed cable to form the structure shown in FIG. 13. Note again that no voids are present within the structure.

Figure 14:
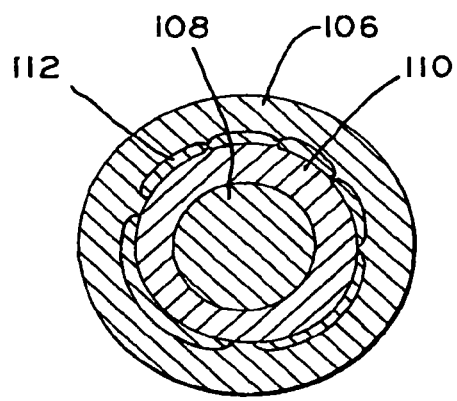
FIG. 14 is a sectional view of a seventh arrangement showing a tube containing a core surrounded by a tube and a plurality of strands.

FIG. 14 shows a still further embodiment. The outside shell or tube 106 is composed of a platinum alloy containing 10% iridium material. Within the tube is a drawn filled tube core formed from a shell 110 of a 35NLT material which is filled with a 41% silver material 108. Surrounding shell 110 are six tantalum RO5200 strands or filaments 112. Elements 108, 110, and 112 are first formed as a cable which is then placed inside shell 106. The entire composite structure is then drawn down to form the structure shown in FIG. 14.

Figure 15:
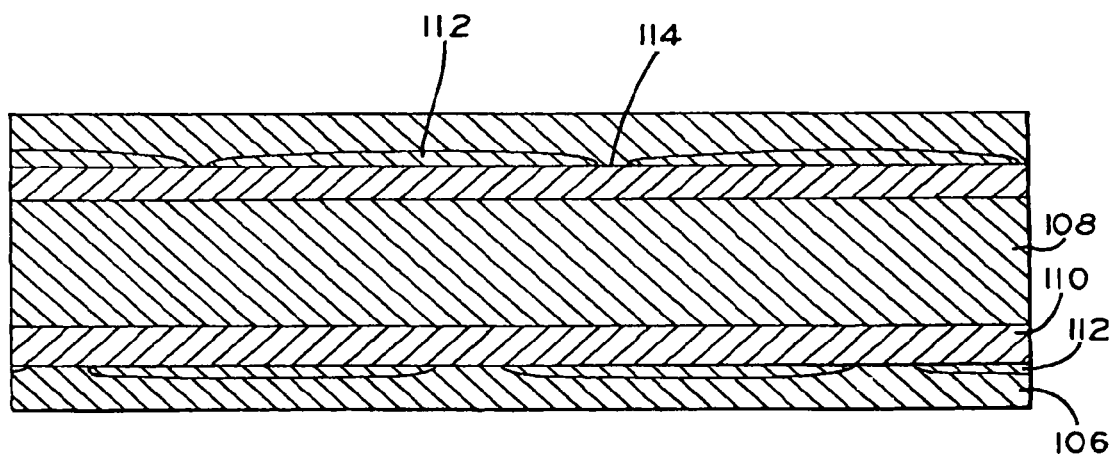
FIG. 15 is a cross sectional view of the structure of the seventh arrangement of FIG. 14 taken along the lengthwise direction of the wire.

FIG. 15 shows a longitudinal section through the wire of FIG. 14. It can be clearly seen in FIG. 15 that tantalum filaments 110 are wound helically around tube 110 as gaps 114 are shown between the various tantalum strands 112.

While this invention has been described as having an exemplary design, the present invention may be further modified within the spirit and scope of this disclosure. This application is therefore intended to cover any variations, uses, or adaptations of the invention using its general principles.

What is claimed is:

1. A metallic wire, comprising:
an outer cylindrical shell of a first biocompatible metal; and
a plurality of wire elements disposed within said shell, at least one of said wire elements including an outer tubing of a second biocompatible metal filled with a core of a third biocompatible metal, said outer shell and said plurality of wire elements compacted together such that substantially no voids exist within said outer shell.

2. The wire of claim 1, wherein said first biocompatible metal comprises platinum or a platinum alloy, said second biocompatible metal comprises an alloy of cobalt, nickel, chromium, and molybdenum, and said third biocompatible metal comprises silver or a silver alloy.

3. The wire of claim 1, wherein said plurality of wire elements are stranded together by twisting.

4. The wire of claim 1, wherein said plurality of wire elements include at least one solid core wire element made of a fourth biocompatible metal and not including said outer tubing.

5. The wire of claim 1, wherein said plurality of wire elements includes at least one hollow tube.

6. The wire of claim 1, including an additional outer cylindrical shell covering said outer shell, said additional outer cylindrical shell made of a fourth metal.

7. The wire of claim 1, including a layer of electrically insulating material at least partially covering said outer shell.

8. A metallic wire, comprising:
an outer cylindrical shell of a first biocompatible metal;
a core element of a second biocompatible metal within said outer shell; and
a plurality of wire elements disposed between said core element and said outer shell, said plurality of wire elements together forming a substantially continuous annular layer between said core element and said outer shell in cross section, said wire elements compacted between said core element and said outer shell such that substantially no voids exist within said outer shell.

9. The wire of claim 8, further comprising an interior wire element disposed within said core element.

10. A metallic wire, comprising:
an outer cylindrical shell of a first biocompatible metal;
a core element of a second biocompatible metal within said outer shell; and
a plurality of wire elements disposed between said core element and said outer shell, said plurality of wire elements together forming a substantially continuous annular layer between said core element and said outer shell in cross section, said wire elements compacted between said core element and said outer shell such that substantially no voids exist within said outer shell, wherein said wire elements each include an outer tubing of a third biocompatible metal with said outer tubing filled with a core of a fourth biocompatible metal.

11. A metallic wire, comprising:
an outer cylindrical shell of a first biocompatible metal;
a core element of a second biocompatible metal within said outer shell; and
a plurality of wire elements disposed between said core element and said outer shell, said plurality of wire elements together forming a substantially continuous annular layer between said core element and said outer shell in cross section, said wire elements compacted between said core element and said outer shell such that substantially no voids exist within said outer shell, wherein said wire elements include:
a plurality of first wire elements each including an outer tubing of a third biocompatible metal with said outer tubing filled with a core of a fourth biocompatible metal; and
a plurality of second wire elements each including a solid core wire element of a fifth biocompatible metal and not including said outer tubing.

12. A method of making a metallic wire, said method comprising the steps of:
providing an outer cylindrical shell of a first biocompatible metal, the shell having a first outer diameter;
inserting a plurality of wire elements into the outer shell to form a wire construct, at least one of the wire elements including an outer tubing of a second biocompatible metal with the outer tubing filled with a core of a third biocompatible metal; and
drawing the wire construct to form a drawn wire of reduced diameter with the outer shell having a second outer diameter less than the first outer diameter, and the plurality of wire elements being compacted together such that substantially no voids exist within the outer shell.

13. The method of claim 12, further comprising, prior to said inserting step, the additional steps of:
forming the plurality of wire elements into a bundle; and
twisting the bundle of wire elements to form a twisted strand.

14. The method of claim 12, further comprising, prior to said inserting step, the additional step of:
twisting the wire elements about a core element wherein, in said inserting step, the core element and the wire elements are both inserted into the outer shell.

15. The method of claim 14, further comprising, prior to said drawing step, the additional step of inserting at least one interior wire element within the core element.

16. The method of claim 12, further comprising, after said drawing step, the additional step of:
coating the drawn wire with an electrically non-conductive insulating material.

17. The method of claim 12, further comprising, prior to said drawing step, the additional steps of:
providing a second outer cylindrical shell of a fourth metal; and
inserting the wire construct into the second outer cylindrical shell.

* * * * *